United States Patent [19]

Madaus et al.

[11] 4,098,883
[45] Jul. 4, 1978

[54] ALUMINUM COMPOUND AND PHARMACEUTICAL COMPOSITIONS CONTAINING SAME

[75] Inventors: Rolf Madaus, Cologne-Brück; Klaus Görler; Werner Stumpf, both of Bensberg-Refrath, all of Germany

[73] Assignee: Dr. Madaus & Co., Cologne-Merheim, Germany

[21] Appl. No.: 664,111

[22] Filed: Mar. 5, 1976

[30] Foreign Application Priority Data

Mar. 12, 1975 [DE] Fed. Rep. of Germany ....... 2510663

[51] Int. Cl.$^2$ .................. A61K 33/06; A61K 33/08; C01B 17/98; C01F 7/74
[52] U.S. Cl. ............................. 424/157; 423/512 R; 423/556; 424/154
[58] Field of Search ............... 424/154, 157; 423/512, 423/556

[56] References Cited

U.S. PATENT DOCUMENTS

| | | | |
|---|---|---|---|
| 3,544,476 | 12/1970 | Aiba et al. | 423/556 |
| 3,911,090 | 10/1975 | Hem et al. | 423/556 |
| 3,929,660 | 12/1975 | Aiba et al. | 423/556 |

OTHER PUBLICATIONS

J.A.C.S., 72, 1282–1286 (1950).
Gamelins Hardbrid, 35 pp. 278–279 (1934).

*Primary Examiner*—Stanley J. Friedman
*Attorney, Agent, or Firm*—Burgess, Dinklage & Sprung

[57] ABSTRACT

A new compound, viz., aluminum polyhydroxysulfate hydrate of the formula $[Al_7(OH)_{17}(SO_4)_2 \cdot n\ H_2O]$ where $n$ equals 10–15, preferably 12, has been found to have outstanding therapeutic value in the treatment of urinary stones; the invention thus provides methods of treating phosphate conditions in the urinary passage and compositions for such treatment comprising said new aluminum compound.

4 Claims, No Drawings

ALUMINUM COMPOUND AND PHARMACEUTICAL COMPOSITIONS CONTAINING SAME

This invention concerns a new compound, pharmaceutical compositions containing it, and a method of treating kidney stones. More specifically, the invention relates to the new compound aluminum polyhydroxysulfate-hydrate having the formula $[Al_7(OH)_{17}(SO_4)_2] \cdot n\ H_2O$, where $n = 10\text{--}15$, preferably 12, together with the method for its manufacture and the medicine containing it.

BACKGROUND

The main difficulty in treating urinary stones is due to the fact that the stone formation itself is a complex process. In the past certain insoluble aluminum compounds, in particular aluminum hydroxide gels and aluminum carbonate gels, have been tested in patients with phosphate stones, but without impressive results, as can be seen from publications such as: E. Hienzsch u. H. J. Schneider, Der Harnstein, Gustav Fischer-Verlag Jena, 1973; E. Shorr u. A. C. Carter, J.A.M.A., 144, 1549-56 (1950); H. Kracht, A. A. Kollwitz, E. Löhe, Der Urologe, S. 1-6 (1970); Th. Friis u. E. Weeke, Acta med. scand., Vol. 187, 41-48 (1970); H. Studer, Helv. Chirurgica Acta, 23, 130 (1956); E. Shorr, Journ., Urolog., 53, 507-(1945); L. S. Goodman u. A. Gilman, The Pharmacological Basis of Therapeutics (4th Edition); M. Lotz et al., New Engl. J. Med. 409-415 (1968); and DOS (German Published Specifications) Nos. 1,921,999; 2,152,228; 2,201,752; and 2,406,120.

The action of these compounds is based upon the reduction of the absorption of phosphate from the diet, because, when aluminum hydroxide gels or aluminum carbonate gels are administered orally, phosphate addition products form in the intestine, which are eliminated with the feces. The unsatisfactory results obtained hitherto with the present method of treatment are due to the fact that the phosphate binding capacities of the aluminum compounds that have been tried have proven to be unreliable and insufficiently active. This is why they have had to be administered in such high doses, and this causes disturbances in the stomach and intestinal tract; often they have produced an undesirable simultaneous binding of stomach acid. Due to their low capacity for the binding of phosphate, these compounds are not easily controllable, so that, if they are administered in large volume they can cause a complete removal of the phosphate from the food the patient consumes, a certain amount of phosphates being necessary in the diet for metabolic equilibrium. The preparations containing these compounds are offered mainly in the form of gels or emulsions, the patient being required to carry about with him and consume unreasonable amounts of medication; in the case of other, dry preparations, the number of tablets that must be consumed is greater than reasonable. Most of the aluminum compounds presently available also undesirably raise the pH of the urine, and thus cause phosphate supersaturation, thereby augmenting the tendency towards crystallization.

Thus, there arises the necessity to create an aluminum compound whose capacity for binding phosphate will be several times higher than that of those known hitherto, one which will produce no appreciable changes in the pH of the stomach, will permit better control, and above all will be usable in smaller amounts in dry product form, and one which will not result in any significant increase in the pH of the urine and will not lose its activity through the aging of the aluminum compound.

THE INVENTION

It has now been found that the new compound, aluminum polyhydroxysulfate hydrate, of the formula $[Al_7(OH)_{17}(SO_4)_2]\ n\ H_2O$, wherein $n$ is equal to 10-15, but preferably 12, complies with these requirements. It is outstandingly suitable for the treatment of persistent phosphatic concretions in the excretory urinary passages, preventing the further growth of such concretions or indirectly causing them to decompose or to be eliminated.

The new aluminum polyhydroxysulfate is prepared by reacting aluminum sulfate with sodium hydrogen carbonate at room temperature, with stirring, in a molar ratio of 1:5 and in a volumetric ratio of 3:5, in aqueous solutions (the concentration of the solutions being limited by the solubility of the sodium hydrogen carbonate) while maintaining a constant pH between 5 and 6 in the reaction mixture. The solutions are combined by pouring them simultaneously into water. (If the above-prescribed molar ratio and proportions and pH are not adhered to, reaction products are obtained which have an unsatisfactory phosphate binding capacity.) The aluminum polyhydroxysulfate that precipitates is in the form of a white, amorphous powder which, after being washed with water until sulfate-free, is dried in a vacuum of 1 to 2 Torr at 50° C. The aluminum polyhydroxysulfate, which is insoluble in water, is free of carbonate and has a weakly acid reation in aqueous suspension. Its phosphate binding capacity amounts to 260 to 300 mg of $PO_4$ per gram of dry substance. Even after long storage under normal conditions, this capacity remains unaffected. The new aluminum polyhydroxysulfate, which is a complex compound of seven nuclei, thus has a phosphate binding capacity that is 10 times that of the previously known and tested aluminum oxides, aluminum hydroxides and aluminum hydroxide gels, and twice that of aluminum carbonate gels.

The degree of hydration is what determines the phosphate binding capacity of the new aluminum polyhydroxysulfate compound of the invention, and it can not be less than 10 molecules of $H_2O$ per molecule; a degree of hydration of 12 molecules of $H_2O$ per molecule has proven very advantageous for the binding of phosphate. If the degree of hydration is less than 10 molecules of $H_2O$ per molecule, the phosphate binding capacity diminishes, and at 6 molecules of $H_2O$ per molecule, it is reduced to only about one-half.

The compound of the invention, of the formula $[Al_7(OH)_{17}(SO_4)_2] \cdot n\ H_2O$, wherein $n$ is equal to 10 to 15, and preferably 12, is characterized by valuable therapeutic properties. It develops an especially strong protective and stone dissolving effect in patients with phosphate stones. In agreement with the high phosphate binding capacities measured in vitro, the clinical tests also showed the superiority of the new aluminum polyhydroxysulfate compound over the previously known aluminum compounds. Several series of tests were performed on fully balanced human subjects (standardized nutrition, equal number of calories per day, equal carbohydrates, equal protein and fat, etc.). They were given 2 grams of aluminum polyhydroxysulfate hydrate four times daily per os and, after an appropriate preliminary period, their 24-hour urine was collected and subjected to analytical tests. The input of phosphate and of nitrogen was also subject to control in the tests.

The therapeutic object was to reduce the phosphate absorption such that the [Ca$^{--}$].[PO$_4^{---}$] solubility product would increase while the phosphate necessary for the metabolism would nevertheless be available. The therapeutic effect can be achieved, without interference with normal metabolic needs, bu use of an input of 0.8 to 2 g of phosphorus per day, i.e., 2.4 to 6.1 g of phosphate per day.

Furthermore, since the solubility of phosphate salts differs according to the pH value of the urine, it is important that the latter be not significantly altered.

In the clinical tests the following procedure was used: a preliminary period of seven days of no medication was followed by a period during which aluminum polyhydroxysulfate was administered. The effect was studied on the basis of the clinico-chemical parameters such as the pH value, and the phosphate and calcium levels, after first examining the factors which might affect the results, such as the period of treatment, the data of the test, and the subject, by means of a variance analysis. Surprisingly, the tests gave the following results to our full satisfaction:

1. Aluminum polyhydroxysulfate hydrate does not significantly alter the pH of the urine, which averaged an increase from 6.28 to 6.39 in contrast to the previously known preparations used as controls in our clinical studies, which produced a marked average increase of the pH from 6.28 to 6.63, for example. This fact is of special importance, since the pH value is what determined the solubility of phosphatic calculi. At a urine pH of 6.0, calcium phosphate is doubly supersaturated, while at a pH of 7, the same salt can be eight times supersaturated; it must be considered in this connection that urine represents a peculiar solvent system with regard to supersaturation. Accordingly, the medicament used in the treatment of calculi must in no case significantly increase the initial pH, since any change in the pH would have an appreciable effect on the solubility of phosphate salts in the urine. This requirement is fulfilled by the new aluminum polyhydroxysulfate hydrate.

2. The phosphate content in the urine diminishes on an average from 17.68 mmoles per 24 hours to 4.34 mmoles per 24 h, which proves that the phosphate binding activity of the remedy used assures the attainment of the desired metabolical effect in the organism.

3. The amount of calcium eliminated with the urine in 24 hours is approximately the same for both test periods (preliminary period, medication period)(average for the preliminary period: 4.80 mmoles per day, medication period: 5.07 mmoles per day), which is advantageous for the calcium balance.

4. An additional advantage of the new aluminum polyhydroxysulfate hydrate compound has proven to be its good overall compatibility. The high dosage used in this clinical test of 2 g four times daily was tolerated without complaint. It is advantageous in this connection that the new drug can be suspended in liquid or can be taken together with liquid nourishment.

Additional proof of good compatibility is lastly the absence of significant effects on stomach acidity after taking the new drug, which is indicated also by the secretion time.

The excellent compatibility is further confirmed by the findings relating to toxicity, as shown by the following experiments:

Wistar rats were kept fasting for 20 hours before administration of the substance. The substance was administered suspended in 1% gum tragacanth solution through a stomach tube. 4 Doses were administered to 4 groups of 10 animals (5 male and 5 female) each, the doses amounting to 100, 1000, 2000 and 4000 mg/kg. The observation time extended over a period of 14 days during which the animals received normal feeding. They were daily examined for health, body weight and temperature.

In another test series the tests were performed on dogs (beagles). The substance, suspended in tap water, was administered through a funnel and stomach tube. In a preliminary test with tap water, no vomiting had been induced in the same experimental animals by the introduction of the stomach tube. The dose given to the first group (12 animals) was 1 gram per kilogram of body weight. In the following 7 days the animals received normal feeding and were daily examined for general health. 8 days after this first administration of the drug, the dogs were divided into 2 groups of 6 each. The doses then were increased to 2.5 and 5 g/kg. The observation time was again 7 days.

In both of the experiments the body temperature and body weight remained normal, so that neither in the rats nor in the dogs could any toxic effects be observed.

EXAMPLES

Examples of Preparation 84 kg of sodium hydrogen carbonate in 1000 liters of water and 133 kg of aluminum sulfate . 18 H$_2$O in 600 l of water were poured into 600 l of water at room temperature over a period of 60 minutes, with vigorous sturring, the pH being adjusted to 5 to 6. The reaction mixture was then stirred for another hour. After this period the pH was 5.4. The product that precipitated was centrifuged and washed with water until free of sulfate; then it was vacuum dried at 50° C for 20 hours. On the basis of the analysis performed, its formula was [Al$_7$(OH)$_{17}$(SO$_4$)$_2$]. 12 H$_2$O. Its phosphate binding capacity amounted to from 260 to 300 mg per gram of dry substance.

The degree of hydration was adjusted on the basis of control measurements performed while the substance was drying. It was not allowed to diminish below 10 molecules of H$_2$O per molecule. Values higher than 15 H$_2$O are unacceptable since, although they do not affect the phosphate binding capacity with respect to the dry substance, they are undersirable for Galenic dry preparations.

The substance was chemically analyzed for identification. Ten different batches were found to have the following sum formula, computed on the basis of the anhydrous substance: Al$_7$(OH)$_{17}$(SO$_4$)$_2$. Furthermore, the determination of the water in the finished, prepared substance in this case showed a content of 12 H$_2$O molecules per molecule, or $n = 12$, i.e., the formula of the substance in this case would be [Al$_7$(OH)$_{17}$(SO$_4$)$_2$ . 12 H$_2$O].

GALENIC EXAMPLE 1

Powder 100 kg of the powdered preparation were prepared in accordance with the following composition:

Aluminum polyhydroxysulfate hydrate prepared

GALENIC EXAMPLE 2

Tablets 600 kg of pressing composition was prepared in accordance with the following composition:

| | |
|---|---|
| Aluminum polyhydroxysulfate hydrate prepared as in the Example of Preparation | 400.000 kg |
| Lactose | 100.000 kg |
| Starch | 85.000 kg |
| Polyvinylpyrrolidone | 10.000 kg |
| Magnesium stearate | 5.000 kg |
| | 600.000 kg |

GALENIC EXAMPLE 3

Gel 100 kg of gel was prepared on the basis of the following formula:

| | |
|---|---|
| Aluminum polyhydroxysulfate hydrate as in the Example of Preparation | 10.000 kg |
| Carboxymethylcellulose, sodium salt | 1.450 kg |
| as in the Example of Preparation | 40.000 kg |
| Sorbitol | 32.900 kg |
| Saccharose | 27.000 kg |
| Flavoring | 0.100 kg |
| | 100.000 kg |

| | |
|---|---|
| Glycerine | 1.400 kg |
| p-Hydroxybenzoic acid ester | 0.200 kg |
| Saccharine sodium | 0.010 kg |
| Demineralized water   to make | 100.000 kg |

It will be understood that the specification and examples are illustrative but not limitative of the present invention and that other embodiments within the spirit and scope of the invention will suggest themselves to those skilled in the art.

What is claimed is:

1. Aluminum polyhydroxysulfate hydrate of the formula $[Al_7(OH)_{17}(SO_4)_2] \cdot n\, H_2O$, wherein $n$ is an integer from 10 to 15.

2. Aluminum polyhydroxysulfate hydrate as claimd in claim 1 wherein $n$ is 12.

3. Method of preparing the compound of claim 1 comprising reacting aluminum sulfate and sodium hydrogen carbonate in a molar ratio of 1:5 in aqueous solutions in a volume ratio of 3:5 at room temperature with stirring, while maintaining a pH range between 5 and 6, pouring the solutions simultaneously into water, washing the reaction product that precipitates sulfate-free with water, and drying same at 50° C in vacuo at 1 to 2 mm Hg.

4. Pharmaceutical composition comprising a pharmaceutically acceptable carrier and, in an amount effective to combat phosphate conditions in the urinary passage, aluminum polyhydroxysulfate hydrate of the formula $[Al_7(OH)_{17}(SO_4)_2] \cdot n\, H_2O$ wherein $n$ is an integer from 10 to 15, as claimed in claim 1.

* * * * *